US010947262B2

(12) United States Patent
Gronke et al.

(10) Patent No.: US 10,947,262 B2
(45) Date of Patent: Mar. 16, 2021

(54) HYDROPHOBIC INTERACTION CHROMATOGRAPHY FOR PURIFICATION OF OLIGONUCLEOTIDES

(71) Applicant: BIOGEN MA INC., Cambridge, MA (US)

(72) Inventors: Robert S. Gronke, Cambridge, MA (US); Ratnesh S. Joshi, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/309,622

(22) PCT Filed: Jun. 13, 2017

(86) PCT No.: PCT/US2017/037126
§ 371 (c)(1),
(2) Date: Dec. 13, 2018

(87) PCT Pub. No.: WO2017/218454
PCT Pub. Date: Dec. 21, 2017

(65) Prior Publication Data
US 2019/0248823 A1 Aug. 15, 2019

Related U.S. Application Data

(60) Provisional application No. 62/492,402, filed on May 1, 2017, provisional application No. 62/349,970, filed on Jun. 14, 2016.

(51) Int. Cl.
| | | |
|---|---|---|
| *C07H 1/06* | (2006.01) | |
| *C07H 1/00* | (2006.01) | |
| *B01D 15/30* | (2006.01) | |
| *B01D 15/42* | (2006.01) | |
| *C07H 21/02* | (2006.01) | |
| *C07H 21/04* | (2006.01) | |

(52) U.S. Cl.
CPC .............. *C07H 1/06* (2013.01); *B01D 15/305* (2013.01); *B01D 15/426* (2013.01); *C07H 1/00* (2013.01); *C07H 21/02* (2013.01); *C07H 21/04* (2013.01)

(58) Field of Classification Search
CPC ...... B01D 15/305; B01D 15/426; C07H 1/00; C07H 1/06; C07H 21/02; C07H 21/04
See application file for complete search history.

(56) References Cited

U.S. PATENT DOCUMENTS

| | | | |
|---|---|---|---|
| 6,087,491 A | 7/2000 | Tang et al. | |
| 6,310,198 B1 * | 10/2001 | Tang | ................ C07H 21/00 |
| | | | 435/6.1 |
| 7,169,917 B2 * | 1/2007 | de Franca Teixeira dos Prazeres | ............ A61K 48/00 |
| | | | 210/635 |

FOREIGN PATENT DOCUMENTS

| | | |
|---|---|---|
| WO | 1996/01268 A1 | 1/1996 |
| WO | 2004/020449 A1 | 3/2004 |

OTHER PUBLICATIONS

Ramage et al., 4-(17-tetrabenzo[a,c,g,i]fluorenylmethyl)-41',4?-Dimethoxytrityl Chloride: A hydrophobic 5'-protecting group for the separation of synthetic oligonucleotides. Tetrahedron Letters. Oct. 29, 1993;34(44):7133-7136.
International Search Report and Written Opinion for Application No. PCT/US2017/037126, dated Oct. 23, 2017, 13 pages.

* cited by examiner

*Primary Examiner* — Lawrence E Crane
(74) *Attorney, Agent, or Firm* — McCarter & English, LLP; Steven G. Davis; Xin Zhang

(57) ABSTRACT

The invention herein describes a method to purify a target oligonucleotide using hydrophobic interaction chromatography (HIC). The method includes adding a salt to a mixture of the target oligonucleotide and product-related impurities, applying the diluted mixture, at a particular dynamic loading capacity, to the hydrophobic interaction chromatography resin (or hydrophobic adsorbent), washing the hydrophobic adsorbent with an aqueous salt solution, eluting the target oligonucleotide with a eluting solution, and collecting the eluent comprising the target oligonucleotide.

18 Claims, 3 Drawing Sheets
Specification includes a Sequence Listing.

HYDROPHOBIC INTERACTION CHROMATOGRAPHY FOR PURIFICATION OF OLIGONUCLEOTIDES

REFERENCE TO RELATED APPLICATIONS

This application is a 35 U.S.C. § 371 national stage filing of International Application No. PCT/US2017/037126, filed on Jun. 13, 2017, which claims the benefit of the filing date under 35 U.S.C. § 119(e), of U.S. Provisional Application No. 62/349,970, filed on Jun. 14, 2016, and U.S. Provisional Application No. 62/492,402, filed on May 1, 2017. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jun. 12, 2017, is named 123429-00120_SL.txt and is 839 bytes in size.

BACKGROUND OF THE INVENTION

Oligonucleotides are short DNA or RNA oligomers that can be chemically synthesized for research and medical purposes. Oligonucleotides are typically prepared by a stepwise addition of nucleotide residues to produce a specific sequence. During the synthesis, inefficiencies at any of the steps are possible, resulting in an oligomer either missing a nucleoside ("the N−1 impurity") or having a phosphodiester bond instead of the desired phosphothioester bond ("the P=O impurity"). In addition, exposure to oxidative conditions during or after the synthesis could convert a P=S bond to a P=O bond to form a P=O impurity. Following completion of the synthesis of the oligonucleotide of the desired sequence, the target oligonucleotide is obtained as a mixture along with all of the failed sequences and the N−1 and P=O impurities. These impurities then need to be separated from the target oligonucleotide.

One commonly used separation technique is reverse-phase high pressure liquid chromatography (rp-HPLC) is used to purify oligonucleotides, however, rp-HPLC generally cannot effectively remove the N−1, the P=O, the ABasic, the CNEt and/or the N+1 impurities. Another disadvantage of rp-HPLC includes the use of significant amount of organic solvents, which creates a disposal issue and as well as the need to conduct the purification in an explosion proof facility.

Therefore, purification methods for oligonucleotides that can remove the N−1, the P=O, the ABasic, the CNEt and/or the N+1 impurities and are suitable for a large scale commercial process are needed.

SUMMARY OF THE INVENTION

The invention herein describes a method to purify a target oligonucleotide using hydrophobic interaction chromatography (HIC). In particular, the method described herein includes applying, at a particular dynamic loading capacity, a mixture of the target oligonucleotide and product-related impurities to the hydrophobic interaction chromatography resin (or hydrophobic adsorbent). The claimed method results in an improved separation of the N−1 and P=O impurities from the target oligonucleotide as well as the elimination of the use of organic solvents during the purification process. In certain embodiments, the claimed method can also remove the ABasic, the CNEt and/or the N+1 impurities.

DETAILED DESCRIPTION

Figure 1:
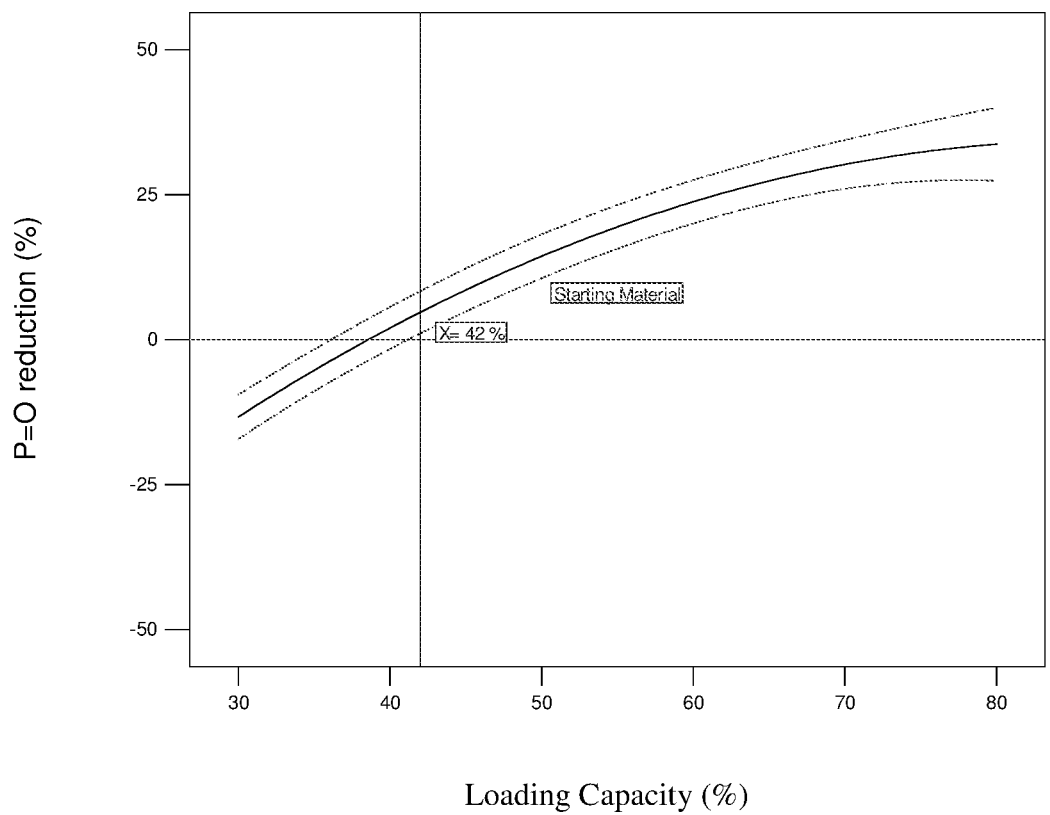
FIG. 1 is a plot depicting the relationship between dynamic loading capacity and removal of the P=O impurity.

The present invention is directed to methods for separating an oligonucleotide from a product related impurities generated during the synthesis of the oligonucleotide. The new process was developed in which a crude oligonucleotide mixture, which contains not only the target oligonucleotide, but also various product related impurities, is applied to a hydrophobic adsorbent at a particular dynamic loading capacity. This new method results in an improved removal of certain product related impurities including the N−1 impurity and the P=O impurity. Such an improvement was surprising because the hydrophobicity of the target oligonucleotide as compared to its N−1 and P=O impurities are expected to be similar and these impurities are not removed by process-scale rp-HPLC, which also relies on hydrophobic interactions. In certain embodiments, the claimed method can also remove the ABasic impurities, the CNEt impurities and the N+1 impurities that are difficult to be removed by rp-HPLC.

A first embodiment of the invention is a method for separating a target oligonucleotide from a mixture containing the target oligonucleotide and a product-related impurity, the method comprising the steps of:
 a) adding salt to the mixture;
 b) contacting the diluted mixture with a hydrophobic adsorbent at a dynamic loading capacity of about 32 to about 78% of the capacity of the hydrophobic adsorbent;
 c) washing the hydrophobic adsorbent with an aqueous salt solution;
 d) eluting the target oligonucleotide with a eluting solution; and
 e) collecting the eluent comprising the target oligonucleotide;
 wherein the product-related impurity includes at least one N−1 impurity, thereby separating the target oligonucleotide from the product-related impurity.

A second embodiment of the invention is a method for separating a target oligonucleotide from a mixture containing the target thiolated oligonucleotide and a product-related impurity, the method comprising the steps of:
 a) adding salt to the mixture;
 b) contacting the diluted mixture with a hydrophobic adsorbent at a dynamic loading capacity of about 40 to about 100% of the capacity of the hydrophobic adsorbent;
 c) washing the hydrophobic adsorbent with an aqueous salt solution;
 d) eluting the target oligonucleotide with a eluting solution; and
 e) collecting the eluent comprising the target oligonucleotide;

wherein the product-related impurity includes at least one P=O impurity, thereby separating the target oligonucleotide from the product-related impurity.

As used herein, a "product-related impurity" refers to the unwanted byproducts generated during the synthesis of the target oligonucleotide. In certain embodiments, a product-related impurity is a i) N−1 impurity; ii) a P=O impurity; iii) or a combination thereof; or iv) a mixture of any of these three. As used herein, "N−1 impurity" is an oligonucleotide that is missing 1 nucleoside at any position relative to the target oligonucleotide due to a failed coupling reaction. As used herein, "P=O impurity" is an oligonucleotide that contains a phosphodiester linkage in place of a desired phosphorothioate linkage of the target oligonucleotide due to a failed sulfurization reaction or unintended oxidation following the synthesis. In certain embodiments, the method as described for the first embodiment can be used to remove the P=O impurity along with the N−1 impurity. In certain embodiments, the method as described for the second embodiment can be used to remove the N−1 impurity along with the P=O impurity.

In certain embodiments, the product-related impurities can also include an ABasic impurity, a CNEt and/or a N+1 impurities. As used herein, a "N+1 impurity" is an oligonucleotide that has 1 additional nucleoside at any position relative to the target oligonucleotide. As used herein, an "ABasic impurity" is an oligonucleotide having one or more nucleosides that are missing the nucleobase as compared to the target oligonucleotide, wherein the nucleoside has the structure shown below:

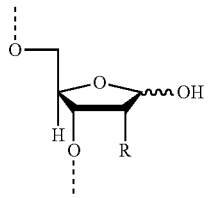

Figure 3:
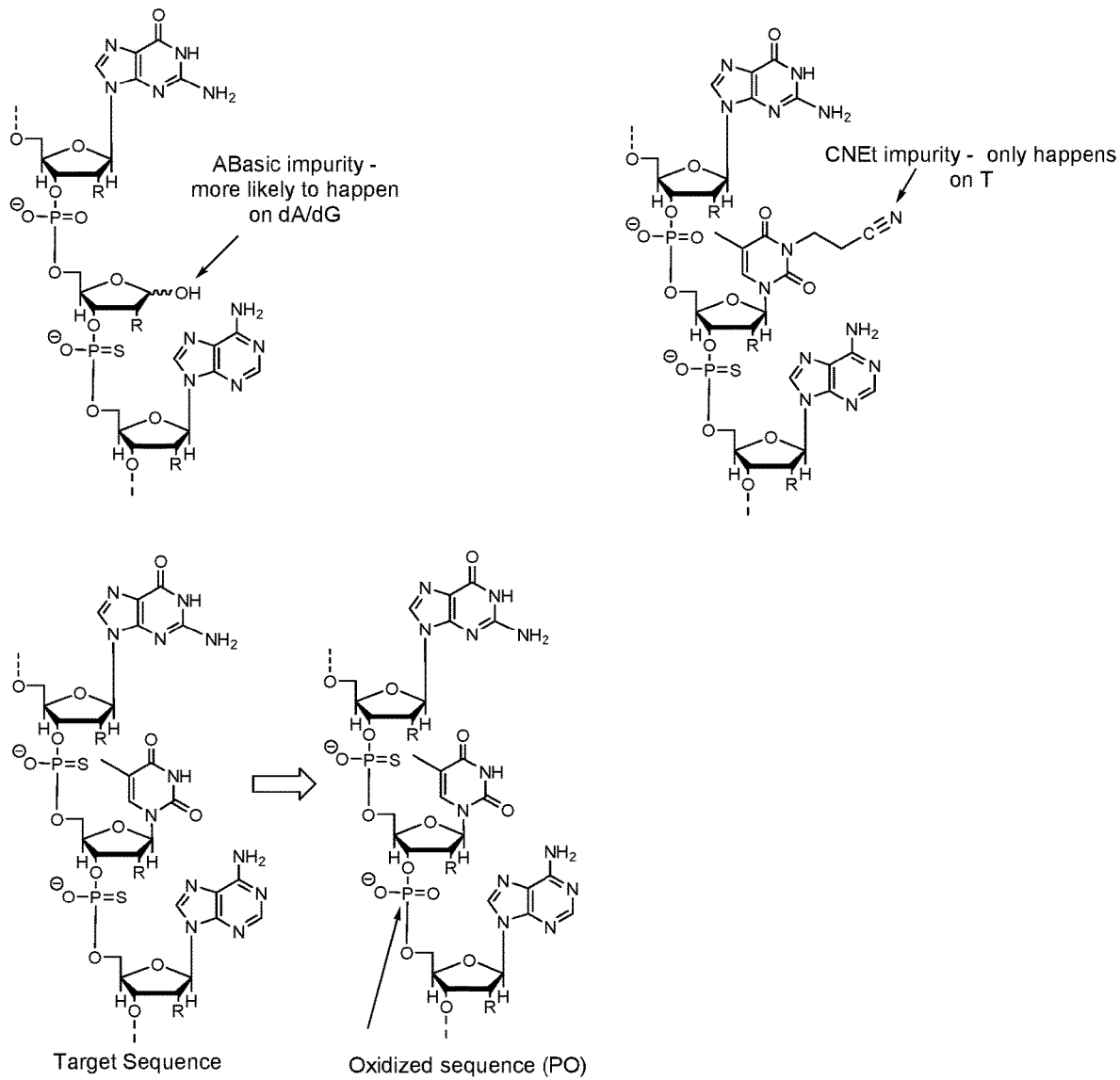
FIG. 3 depicts the exemplary structures of ABasic, CNEt and P=O impurities.

An exemplary structure for an ABasic impurity is shown in FIG. 3. In a particular embodiment, the missing nucleobase in the ABasic impurity is adenosine and/or guanine. As used herein, a "CNEt" impurity is an oligonucleotide that contains a modified thymine nucleobase in place of the unmodified thymine nucleobase of the target oligonucleotide, wherein the modified thymine nucleobase has the following structure:

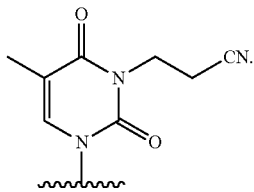 [SMILES: *n1cc(C)c(=O)n(CCC#N)c1=O]

An exemplary structure for CNEt impurity is shown in FIG. 3.

In certain embodiments, the product-related impurities includes a shortmer impurity. As used herein, a "shortmer impurity" is an oligonucleotide that is missing 1, 2, 3, 4, or more nucleosides at any position relative to the target oligonucleotide.

In certain embodiments, the product-related impurities includes an earlier-eluting impurity (EEI). As used herein, the "earlier-elution impurity" is an impurity that elutes before the target oligonucleotide using the purification methods described herein. In one embodiment, the EEI includes a shortmer impurity, such as a N−1 impurity, a P=O impurity, and/or an ABasic impurity.

In certain embodiments, the product-related impuritiy includes a later-eluting impurity (LEI). As used herein, the "later-eluting impurity" is an impurity that elutes after the target oligonucleotide using the purification methods described herein. In one embodiment, the LEI includes the N+1 impurity.

"Oligonucleotide" means a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA). In certain embodiments, the oligonucleotide includes only RNA, only DNA or includes both RNA and DNA. In a particular embodiment, the target oligonucleotide is a gapmer. A "gapmer" means a chimeric compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. In certain embodiments, the target oligonucleotide comprises 10 to 100, 10 to 50, 10 to 25, 15 to 100, 15 to 50, or 15 to 25 nucleotides.

"Nucleoside" means a compound comprising a nucleobase and a sugar moiety. Nucleosides include, but are not limited to, naturally occurring nucleosides, modified nucleosides, and nucleosides having mimetic bases and/or sugar groups. "Modified nucleoside" a nucleoside comprising at least one modification compared to naturally occurring RNA or DNA nucleosides. Such modification may be at the sugar moiety and/or at the nucleobase. Nucleosides may be modified with any of a variety of substituents on either the nucleobase or the sugar moiety.

A "nucleotide" refers to a nucleoside comprising a linking group, which links two nucleosides together as part of the oligonucleotide. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH₂—N(CH₃)—O—CH₂—), thiodiester (—O—C(O)—S—), thionocarbamate (—O—C(O)(NH)—S—); siloxane (—O—Si(H)₂—O—); and N,N'-dimethylhydrazine (—CH₂—N(CH₃)—N(CH₃)—). In a particular embodiment, the linking group is a phosphodiester (P=O) or a phosphorothioate (P=S). In certain embodiments, the target oligonucleotide of the methods described for the first and second embodiments includes only phosphodiesters (P=O), phosphorothioates (P=S), or a combination thereof as the linking group.

A "nucleobase" means the heterocyclic base portion of a nucleoside. In certain embodiments, a nucleobase may comprise any atom or group of atoms capable of hydrogen bonding to a nucleobase of another nucleic acid. Nucleobases may be naturally occurring or may be modified. In addition to "unmodified" or "natural" nucleobases such the purine nucleobases adenine (A) and guanine (G), and the pyrimidine nucleobases thymine (T) (or 5-methyl uracil), cytosine (C) and uracil (U), many modified nucleobases or nucleobase mimetics known to those skilled in the art are amenable to incorporation into the target oligonucleotides as separated by either the method described in the first or second embodiments, including, for example, hypoxanthine, xanthine, 7-methyl guanine, 5,6-dihydrouracil, 5-methylcytosine, 7-deaza purine and 5-hydroxymethylcytosine. In certain embodiments, the method is as described for the first or second embodiment, and the nucleobase is selected from adenine, guanine, thymine (5-methyl uracil), and 5-methylcytosine.

"Sugar moiety" means a natural or modified sugar or sugar surrogate.

"Natural sugar" means a ribofuranose moiety of DNA (2'-H) or RNA (2'-OH).

"Modified sugar" means a ribofuranose moiety comprising at least one substituent other than that of a natural sugar. Such modifications include without limitation, addition of substituent groups, bridging of non-geminal ring atoms to form a bicyclic nucleic acid (BNA), replacement of the ribosyl ring oxygen atom with S, N(R), or $C(R^1)(R)^2$ (R=H, $C_1$-$C_{12}$ alkyl or a protecting group) and combinations of these such. In certain embodiments, the sugar is modified at the 2'-position to include a substituent other than H or OH ("2'-modified" or "2'-substituted"). Alternatively, the modification is at the 5'-position of the sugar. In certain embodiments, the sugar is modified at the 2'-position and the 5'-position of the sugar.

Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted C1 to C10 alkyl or C2 to C10 alkenyl and alkynyl. In certain embodiments, such substituents are selected from among: a halide (including, but not limited to F), allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. In particular, the modified nucleosides suitable for use in the methods described in the first and second embodiments are: 2'-methoxyethoxy ("MOE" or "2'-MOE" or "2'-OCH$_2$CH$_2$OCH$_3$), 2'-O-methyl ("2'-OMe" or 2'-O—CH$_3$), or 2'-fluoro (2'-F).

In certain embodiments, modified nucleosides having a substituent group at the 2'-position selected from: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH$_2$)$_n$ON [CH$_2$)$_n$CH$_3$]$_2$, where n and m are independently from 1 to about 10. Other 2'-sugar substituent groups include: $C_1$ to $C_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocyclyl, and aminoalkylamino.

In certain embodiments, modified nucleosides having a substituent group at oxygen atom at the 5'-position selected from acetyl (Ac); benzoyl (Bz); benzyl (Bn); β-methoxyethoxymethyl ether (MEM); dimethoxytrityl, [bis-(4-methoxyphenyl)phenylmethyl] (DMT); methoxymethyl ether (MOM); methoxytrityl [(4-methoxyphenyl)diphenylmethyl, MMT); p-methoxybenzyl ether (PMB); methylthiomethyl ether; pivaloyl (Piv); tetrahydropyranyl (THP); tetrahydrofuran (THF); trityl (triphenylmethyl, Tr); silyl ether (including, but not limited to, trimethylsilyl (TMS), tert-butyldimethylsilyl (TBDMS), tri-iso-propylsilyloxymethyl (TOM), and triisopropylsilyl (TIPS) ethers); methyl ethers, ethoxyethyl ethers (EE), and 5'-O-(α-methyl-6-nitropiperonyloxycarbonyl) (MeNPOC). In a particular embodiment, the 5' position is —ODMT.

Examples of nucleosides having modified sugar moieties include without limitation nucleosides comprising 5'-vinyl, 5'-methyl, 5'-ODMT, 4'-S, 2'-F, 2'-OCH$_3$ and 2'-O(CH$_2$)$_2$OCH$_3$ substituent groups.

In certain embodiments, 2'-sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl. The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl. An "arylalkyl" is a aryl group linked via an alkylene linker to the reminder of the molecule. An "alkaryl" is a alkyl group linked via an arylene linker to the reminder of the molecule.

As used herein, the term "heterocyclyl" refers to a saturated or unsaturated, monocyclic or bicyclic (e.g., bridged or spiro ring systems) ring system which has from 3- to 7-ring members, or in particular 3- to 6-ring members or 5- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5 or 6 membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or-7-membered bicyclic ring. The heterocyclyl group can be attached at a heteroatom or a carbon atom.

"Bicyclic nucleoside" or "BNA" means a nucleoside wherein the sugar moiety of the nucleoside comprises a bridge connecting two carbon atoms of the sugar ring, thereby forming a bicyclic sugar moiety. Examples of BNAs include without limitation nucleosides comprising a bridge between the 4' and the 2' ribosyl ring atoms ("4'-2' bicyclic nucleoside"), for example, a furanose ring comprising a bridge connecting two carbon atoms of the furanose ring to connect the 2' carbon atom and the 4' carbon atom of the sugar ring.

In certain embodiments, the target oligonucleotide includes one or more BNA nucleosides wherein the bridge comprises one of the formulas: 4'-β-D-(CH$_2$)—O-2' (β-D-LNA); 4'-(CH$_2$)—S-2; 4'-α-L-(CH$_2$)—O-2' (α-L-LNA); 4'-(CH$_2$)$_2$—O-2' (ENA); 4'-C(CH$_3$)$_2$—O-2' (see PCT/US2008/068922); 4'-CH(CH$_3$)—O-2' ("cEt") and 4'-C—H (CH$_2$OCH$_3$)—O-2' (see U.S. Pat. No. 7,399,845, issued on Jul. 15, 2008); 4'-CH$_2$—N(OCH$_3$)-2' (see PCT/US2008/064591); 4'-CH$_2$—O—N(CH$_3$)-2' (see published U.S. Patent Application US2004-0171570, published Sep. 2, 2004); 4'-CH$_2$—N(R)—O-2' (see U.S. Pat. No. 7,427,672, issued on Sep. 23, 2008); 4'-CH$_2$—C(CH$_3$)-2' and 4'-CH$_2$—C(=CH$_2$)-2' (see PCT/US2008/066154); and wherein R is, independently, H, C$_1$-C$_{12}$ alkyl, or a protecting group. In certain embodiments, the present invention provides modified nucleosides comprising modified sugar moieties that are not bicyclic sugar moieties.

"Sugar surrogate" means a structure other than a ribofuranose ring which is capable of substituting for the sugar of a nucleoside. Examples of sugar surrogates include, but are not limited to, 6-membered rings, sugars in which the oxygen is replaced with, for example, sulfur or nitrogen, to form, for example, morpholinos and 4'-thio-containing sugars.

In certain embodiments, the target oligonucleotide separated by the method as described in either the first or second embodiment is a phosphorothioate oligonucleotide having a sequence of (from 5' to 3')

TCACTTTCATAATGCTGG, (SEQ ID NO: 1)

wherein each internucleoside linkage of the oligonucleotide is a phosphorothioate linkage, each nucleoside of the oligonucleotide is a 2'-methoxyethyl (MOE) nucleoside, and each cytosine is a 5'-methylcytosine. SEQ ID NO: 1 is also known as BIIB058, and is described in WO2007/002390, WO2010/148249, and U.S. Pat. No. 8,980,853, the teaching of each are herein incorporated by reference.

In certain embodiments, the target oligonucleotide separated by the method as described in either the first or second embodiment is a 5-10-5 MOE gapmer, having a sequence of (from 5' to 3')

CAGGATACATTTCTACAGCT, (SEQ ID NO: 2)

wherein each of nucleosides 1-5 and 16-20 are 2'-O-methoxyethylribose modified nucleosides, and each of nucleosides 6-15 are 2'-deoxynucleosides, wherein the internucleoside linkages between nucleosides 2 to 3, 4 to 5, 16 to 17, and 18 to 19 are phosphodiester linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 17 to 18, and 19 to 20 are phosphorothioate linkages, and wherein each cytosine is a 5'-methylcytosine. SEQ ID NO: 2 is described by the following chemical notation: mCes Aeo Ges Geo Aes Tds Ads mCds Ads Tds Tds Tds mCds Tds Ads mCeo Aes Geo mCes Te; wherein, A=an adenine,
mC=a 5'-methylcytosine
G=a guanine,
T=a thymine,
e=a 2'-0-methoxyethylribose modified sugar,
d=a 2'-deoxyribose sugar,
s=a phosphorothioate internucleoside linkage, and
o=a phosphodiester internucleoside linkage.

SEQ ID NO: 2 is as known as BIIB067 or ISIS 666853 and is described in WO2015153800, the teachings of which are incorporated herein by reference.

The hydrophobic adsorbent (i.e., "hydrophobic resin") is any material to which the target oligonucleotide will bind such that it can be separated from the product-related impurities in the method as described in the first and second embodiments. For example, the hydrophobic adsorbent include hydrophilic carbohydrates: cross-linked agarose and synthetic copolymer materials. In particular, the hydrophobic adsorbent comprises either phenyl, butyl or hexyl. For example, Hexyl650C is a suitable hydrophobic adsorbent. Furthermore, the hydrophobic adsorbent is packed at a bed height of at least 15 cm, for example at least 20 cm, at least 25 cm, or at least 30 cm; or from about 15 cm to about 30 cm; from about 15 cm to 20 cm, from about 20 to about 25 cm, or about 25 cm to about 30 cm.

The "dynamic loading capacity" is defined as the amount of product (e.g., oligonucleotide product) that will bind to a chromatography resin under typical flow conditions and is determined under specific flow conditions and the loading salt concentration, among other loading factors known to one of skill in the art. It is calculated based on the amount that can be loaded before product levels are measured in the flow through (referred to as the "breakthrough point"). In particular, the material to be separated is applied to the resin in a flowing fashion (as opposed to static done in a batch mode) at a particular flow rate, for example, about 100 to about 250 cm/hr, and in particular, 200 cm/hr. One of skill in the art would know how to select both the salt concentration based on the product's solubility in that salt and the flow rate based on the bead size, bed height and other variables such that the inlet pressure is not exceeded to achieve a particular dynamic loading ratio.

For example, if the capacity of a hydrophobic adsorbent for the oligonucleotide mixture is 50 mg/mL (dynamic), application of 50 mg/mL of the mixture would be at 100% dynamic loading capacity. Similarly, for a 50 mg/mL hydrophobic adsorbent, application of 25 mg/mL of the mixture would be at 50% dynamic loading capacity. For the method as described in the first embodiment, the dynamic loading capacity is about 32% to about 78%, for example, about 32% to about 45%, about 40% to about 50%, about 45% to about 55%, about 50% to about 60%, about 55% to about 65%, about 60 to about 70%, about 65% to about 78%, or about 32% to about 50%, about 40 to about 75%, or about 50% to about 78%. For the method as described in the second embodiment, the dynamic loading capacity is about 40% to about 100%, for example, about 40% to about 50%, about 50% to about 60%, about 60% to about 70%, about 70% to about 80%, about 80% to about 90%, about 90 to about 100%, about 40% to about 75%, or about 40% to about 60%, or about 40% to about 80%. For the method as described in both the first and second embodiments, the dynamic loading capacity is about 40% to about 78%, for example, about 40% to about 45%, about 45% to about 50%, about 50% to about 55%, about 55% to about 60%, about 60% to about 65%, about 65 to about 70%, about 70% to about 75%, or about 40% to about 50%, about 40 to about 75%, or about 50% to about 78%.

In a third embodiment, the method is as described for either the first or second embodiment, and salt is added to the mixture as aqueous salt solution or the salt is dissolved directly into the mixture. In particular, the salt includes any cation of $NH_4^+$, $K^+$ or $Na^+$ and any anion comprised of $F^-$, $[SO_4]^{-2}$, $[HPO_4]^{-2}$, acetate or $Cl^-$ or combinations thereof. Specifically, the salt is ammonium sulfate.

In a fourth embodiment, the method is as described for any of the first, second, or third embodiments, wherein the flow rate of the wash step is slower than the loading flow rate. In particular, the flow rate of the loading step is from about 150 cm/hr to about 250 cm/hr and the flow rate of the wash step is from about 50 cm/hr to about 150 cm/hr, for example, the flow rate of the loading step is from about 175 cm/hr to about 225 cm/hr and the flow rate of the wash step is from about 75 cm/hr to about 125 cm/hr. In particular, the flow rate of the loading step is from about 200 cm/hr and the flow rate of the wash step is from about 100 cm/hr.

In a fifth embodiment, the method is as described for any of the first, second, third, or fourth embodiments, the eluting solution is selected from water, an aqueous salt solution, ethylene glycol, or propylene glycol or mixtures thereof. In particular, the salt includes any cation of $NH_4^+$, $K^+$ or $Na^+$ and any anion comprised of $F^-$, $[SO_4]^{-2}$, $[HPO_4]^{-2}$, acetate or $Cl^-$ or combinations thereof. Specifically, the salt is ammonium sulfate.

In a sixth embodiment, the method is as described for any of the first, second, third, fourth, or fifth embodiments, wherein the elution collection is delayed such that it does not include the first 2-25%, the first 2-10%, the first 2-8%, the first 4-6%, the first 5-10% or the first 10-25% of the product elution peak. In a more specific embodiment, the collection is delayed such that it does not include the first 5% of the product elution peak. In particular, the eluent is collected in fractions and the fraction size is adjusted to separate the target oligonucleotide from the product-related impurities in separate fractions. The fraction size can be readily determined by a skilled person in the art, depending partly on the difference in elution time between the oligonucleotide and the product-related impurity, the amount of the crude product containing the target oligonucleotide and the product-related impurities to be separated, etc.

Also in the sixth embodiment, the method is as described for any of the first, second, third, fourth, or fifth embodiments, wherein the elution collection does not include the first and the last 2-25% of the product elution peak. More specifically, the elution collection does not include the first and the last 2-10%, the first and the last 2-8%, the first and the last 4-6%, the first and the last 5-10% or the first and the last 10-25% of the product elution peak. In another specific embodiment, the elution collection doe not include the first and the last 5% of the product elution peak.

In one embodiment, the wash solution is kept constant during the wash step, known as isocratic wash mode. Alternatively, the washing solution is varied during the wash step, known as gradient wash mode. In gradient wash, the wash solution can be varied from high ionic strength or polarity to low ionic strength or polarity. The decrease in polarity or ionic strength can be achieved by decreasing the salt concentration of the aqueous solution or increasing the volume ratio of the more polar solvent, e.g., water, or other polar solvents, e.g., ethylene or propylene glycol to the higher salt solution. Alternatively, the wash solution can be varied from low polarity or high ionic strength to high polarity or low ionic strength. In another alternative, a gradient wash step can be followed by an isocratic wash step, or vice versa.

In one embodiment, the eluting solution is kept constant during the elution, known as isocratic elution mode. Alternatively, the eluting solution is varied during elution, known as gradient elution mode. In gradient elution, the eluting solution can be varied from high ionic strength or low polarity to low ionic strength or high polarity. The increase in polarity or decrease in ionic strength can be achieved by decreasing the salt concentration of the aqueous solution or increasing the volume ratio of the more polar solvent, e.g., water, or other polar solvent, e.g., ethylene or propylene glycol to the higher salt solution. Alternatively, the elution solution can be varied from low polarity or high ionic strength to high polarity or low ionic strength. In another alternative, a gradient elution can be followed by an isocratic elution, or vice versa.

In one embodiment, the method of the present invention described herein can also remove EEI and/or LEI. In another embodiment, the method of the present invention described herein can remove at least one product-related impurities selected from a shortmer impurity, a N+1 impurity, an ABasic impurity, a CNEt impurity, and a P=O impurity. In another embodiment, the method of the present invention described herein can remove a N−1 impurity, a P=O impurity and at least one product-related impurities selected from a shortmer impurity other than the N−1 impurity, a N+1 impurity, an ABasic impurity, and a CNEt impurity. In another embodiment, the method of the present invention described herein can remove a N−1 impurity, a P=O imporiy, a shortmer impurity other than the N−1 impurity, a N+1 impurity, an ABasic impurity, and a CNEt impurity.

"Separating a target oligonucleotide from a mixture containing the target oligonucleotide and a product-related impurity" or "removing a product-related impurity" means removing at least 15%, for example, 20%, 25%, 30%, 35%, 40%, 45%, 50%, 55%, or 60%, of one or more of the product-related impurities described herein, for example the N−1 impurity, the P=O impurity, the ABasic impurity, the CNEt impurity or the N+1 impurity from the mixture.

EXEMPLIFICATION

Example 1 Removal of the N−1 or P=O Impurity

Materials:
  Column: 6.84 mL Phenyl Sepharose Fast Flow High Sub
  Bed Height: 20 cm
  Product Dilution buffer: 850 mM ammonium sulfate, 50 mM tris, pH 8.5

Equilibration buffer: 800 mM ammonium sulfate, 50 mM tris, pH 8.5
Crude product loading: 765 mM ammonium sulfate, 50 mM tris, pH 8.5
Wash buffer: 440 mM ammonium sulfate, 50 mM tris, pH 8.5
Elution buffer: 40 mM ammonium sulfate, 50 mM tris, pH 8.5
Strip: deionized water
Cleaning in place: 1N sodium hydroxide
Storage: 0.1N sodium hydroxide
UV monitor: 295 nm
Method:
Sample Preparation: The sample (SEQ ID NO: 2) was diluted 10 fold with dilution buffer (final ammonium sulfate concentration is 765 mM)
Cycle method: The column was equilibrated with 4 column volumes (CVs) of 800 mM ammonium sulfate, 50 mM tris, pH 8.5 at 200 cm/hr. The sample was loaded at a rate of 200 cm/hr at three different dynamic loading capacities:
For run 1: loaded at a dynamic loading capacity of 8.8%.
For run 2: loaded at a dynamic loading capacity of 47%.
For run 3: loaded at a dynamic loading capacity of 100%.
The column was washed with 7 CVs of 440 mM ammonium sulfate, 50 mM tris, pH 8.5 at 100 cm/hr. The column was eluted with 6 CVs of 40 mM ammonium sulfate, 50 mM tris, pH 8.5 at 200 cm/hr. The column was stripped with 2 CVs of deionized water at 200 cm/hr. The column was column was cleaned with 3 CVs of 1N sodium hydroxide at 200 cm/hr and stored in 3 CVs of 0.1N sodium hydroxide at 200 cm/hr.
Results:
The relative amount of removal of n−1 and P=O impurities are provided below in Tables 1 and 2, respectively.

TABLE 1

Removal of N − 1 impurity

| Impurity | Starting % Level in Crude | Amount in HIC Eluate at low loading (4 mg/mL) run 1 | Amount in HIC Eluate at medium load (21 mg/mL) run 2 | Amount in HIC Eluate at high load (45 mg/mL) run 3 |
|---|---|---|---|---|
| N − 1 | 3.2 | 3.2 | 2.6 | 4.4 |

TABLE 2

Removal of the P = O impurity

| Impurity | Starting % Level in Crude | Amount in HIC Eluate at low load (4 mg/mL) run 1 | Amount in HIC Eluate at medium load (21 mg/mL) run 2 |
|---|---|---|---|
| P = O | 2.6 | 3.9 | 2.1 |

Based upon the results described in Tables 1 and 2, use of the appropriate dynamic loading capacity is necessary to remove the n−1 and P=O impurities.

Example 2 Relationship Between Dynamic Loading Capacity and P=O Impurity Removal Evaluation of the effect of the dynamic loading capacity on the removal of the P=O product-related impurity was completed using Design of Experiment (DesignExpert™ v9) software. The statistical design type was a central composite. The study type was response surface. 50 runs were performed with a Phenyl Sepharose column of 20 cm bed height and a 45 mg/mL dynamic binding capacity. The wash buffer was 440 mM ammonium sulfate, and the elution buffer was 40 mM ammonium sulfate. Seven and six column volumes of wash and elution buffer were used, respectively. SEQ ID NO: 2 was used as the oligonucleotide, using the same conditions as described above in Example 1.

The results of the analysis demonstrate that for the P=O impurity there is an improvement in the removal of the P=O impurity when a loading capacity of 42%-100% (i.e., 19 mg/mL-45 mg/mL on the chart in FIG. 1).

Figure 2:
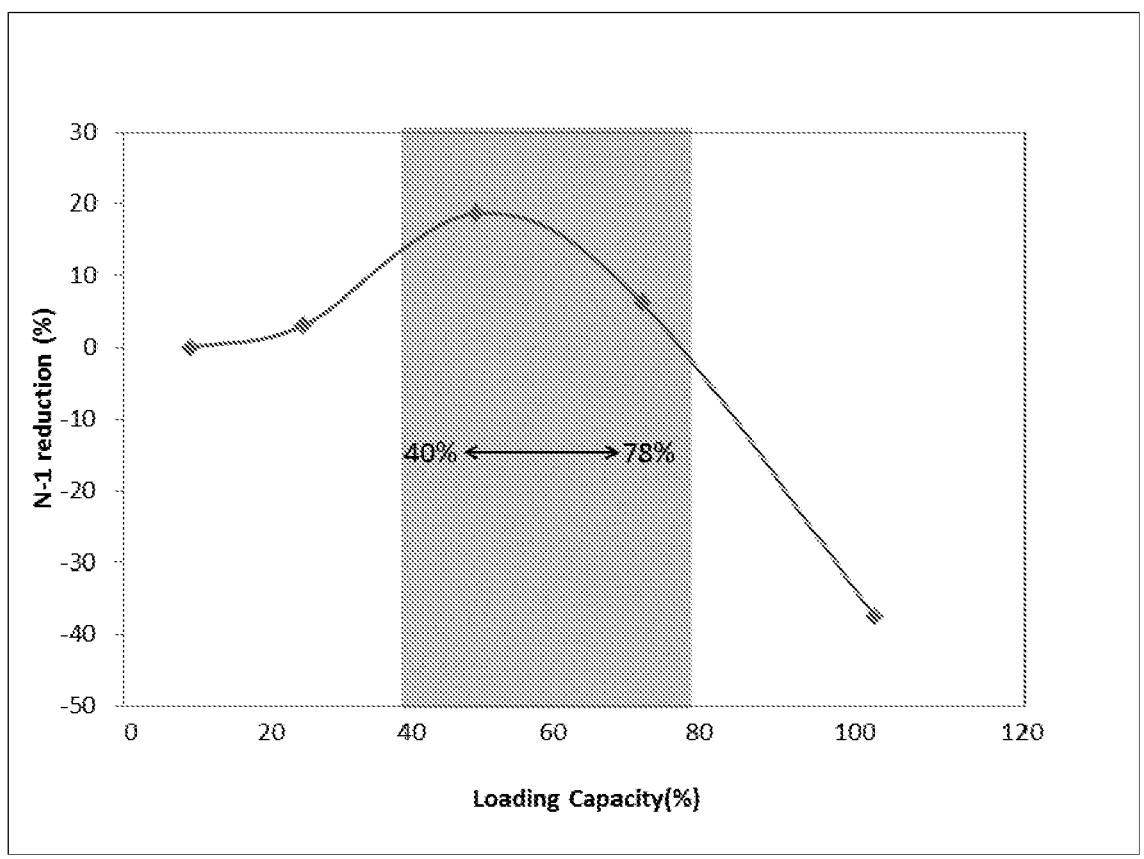
FIG. 2 is a plot depicting the relationship between dynamic loading capacity and removal of the N−1 impurity.

Example 3 Relationship Between Dynamic Loading Capacity and N−1 Impurity Removal Evaluation of the effect of the dynamic loading capacity on the removal of the N−1 product-related impurity is shown in FIG. 2. Five runs are plotted in FIG. 2 and correspond to a loading capacity of 9, 24, 47, 69 and 100% of a 45 mg/mL hydrophobic adsorbent. The percentage of N−1 reduction was calculated from the starting N−1 levels in the crude. The analysis concluded that load ratio is the only factor that is significant in N−1 reduction. Therefore, other variable are insignificant to N−1 reduction according to the statistical analysis.

Materials:
Column: 6.84 mL Phenyl Sepharose Fast Flow High Sub (GE Healthcare Life Sciences, P/C: 17-0973-05).
Bed Height: 20 cm
Product Dilution buffer: 850 mM ammonium sulfate, 50 mM tris, pH 8.5
Equilibration buffer: 800 mM ammonium sulfate, 50 mM tris, pH 8.5
Crude product loading: 765 mM ammonium sulfate, 50 mM tris, pH 8.5
Wash buffers:
440 mM ammonium sulfate, 50 mM Tris, pH 8.5
400 mM ammonium sulfate, 50 mM Tris, pH 8.5
Elution buffer:
40 mM ammonium sulfate, 50 mM Tris, pH 8.5
10 mM ammonium sulfate, 50 mM Tris, pH 8.5
Strip: deionized water
Cleaning in place: 1N sodium hydroxide
Storage: 0.1N sodium hydroxide
UV monitor: 295 nm
Method:
Sample Preparation: The sample (SEQ ID NO: 2) was diluted 10 fold with dilution buffer (final ammonium sulfate concentration is 765 mM).
Cycle method: The column was equilibrated with 4 column volumes (CVs) of 800 mM ammonium sulfate, 50 mM tris, pH 8.5 at 200 cm/hr. The sample was loaded at a rate of 200 cm/hr. at five different loading ratios seen in Table 3.

TABLE 3

DoE Variables for N − 1 reduction based on amount load runs

| Amount Loaded (%) | Wash Buffer (mM Ammonium Sulfate, 50 mM Tris, pH 8.5) | Wash CV | Elution Buffer (mM Ammonium Sulfate, 50 mM Tris, pH 8.5) | Elution CV |
|---|---|---|---|---|
| 9 | 440 | 7 | 40 | 6 |
| 24 | 400 | 10 | 10 | 10 |

TABLE 3-continued

DoE Variables for N − 1 reduction based on amount load runs

| Amount Loaded (%) | Wash Buffer (mM Ammonium Sulfate, 50 mM Tris, pH 8.5) | Wash CV | Elution Buffer (mM Ammonium Sulfate, 50 mM Tris, pH 8.5) | Elution CV |
|---|---|---|---|---|
| 47 | 440 | 7 | 40 | 6 |
| 69 | 400 | 4 | 10 | 2 |
| 100 | 440 | 7 | 40 | 6 |

The column was washed at 100 cm/hr with the specified wash buffer and CVs in Table 3. The column was eluted at 200 cm/hr with the specified elution buffer and CVs in Table 3. The column was stripped with 2 CVs of deionized water at 200 cm/hr. The column was column was cleaned with 3 CVs of 1N sodium hydroxide at 200 cm/hr. and stored in 3 CVs of 0.1N sodium hydroxide at 200 cm/hr.

As shown in FIG. 2, there is an improvement in the removal of the N−1 impurity when a loading capacity of 40% to 78%.

Example 4. Removal of the ABasic, CNEt or N+1 Impurity

Materials:
Column: 81 mL packed with Phenyl Sepharose Fast Flow High Sub
Bed Height: 15 cm; Bed Diameter: 2.6 cm
Product Dilution buffer: 575 mM ammonium sulfate, 50 mM tris, pH 8.5
Equilibration buffer: 500 mM ammonium sulfate, 50 mM tris, pH 8.5
Crude product loading: 500 mM ammonium sulfate, 50 mM tris, pH 8.5
Wash buffer: 250 mM ammonium sulfate, 50 mM tris, pH 8.5
Elution buffer: 10 mM ammonium sulfate, 50 mM tris, pH 8.5
Strip: water
Cleaning in place: 1N sodium hydroxide
Storage: 0.1N sodium hydroxide
UV monitor: 295 nm
Method:
Sample Preparation: The crude sample (SEQ ID NO: 1) was diluted 7.7 fold with product dilution buffer (final ammonium sulfate concentration is 500 mM)

Chromatography column method: The column was equilibrated with 5 column volumes (CVs) of 500 mM ammonium sulfate, 50 mM tris, pH 8.5 at 150 cm/hr. The diluted crude sample was loaded at a flow rate of 150 cm/hr at a dynamic loading capacity of 47% (26.5 mg product/mL resin).

The column was washed with 7 CVs of 250 mM ammonium sulfate, 50 mM tris, pH 8.5 at 75 cm/hr. The column was eluted with 9 CVs of 10 mM ammonium sulfate, 50 mM tris, pH 8.5 at 150 cm/hr and the peak was collected. The column was stripped with 3 CVs of deionized water at 150 cm/hr. The column was column was cleaned with 3 CVs of 1N sodium hydroxide at 150 cm/hr and stored in 3 CVs of 0.1N sodium hydroxide at 150 cm/hr.

Results:
The relative amount of removal of ABasic, CNEt and N+1 impurities relative to amount in the crude are provided below in Tables 4, 5 and 6, respectively.

TABLE 4

Removal of ABasic impurity

| Impurity | Starting % Level in Crude | % Level in HIC Eluate |
|---|---|---|
| ABasic | 0.34 | 0.19 |

TABLE 5

Removal of the CNEt impurity

| Impurity | Starting % Level in Crude | % Level in HIC Eluate |
|---|---|---|
| N + 1 | 0.31 | 0.20 |

TABLE 6

Removal of the N + 1 impurity

| Impurity | Starting % Level in Crude | % Level in HIC Eluate |
|---|---|---|
| N + 1 | 1.25 | 0.20 |

Based upon the results described in Tables 4, 5 and 6, loading the HIC column in the center of its dynamic binding capacity allows for removal of the ABasic, CNEt and N+1 impurities.

What is claimed is:

1. A method for separating a target oligonucleotide from a mixture containing the target oligonucleotide and a product-related impurity, the method comprising the steps of:
   a) adding a salt to the mixture, wherein the salt is ammonium sulfate;
   b) contacting the diluted mixture with a hydrophobic adsorbent at a dynamic loading capacity of about 32 to about 78% of the capacity of the hydrophobic adsorbent wherein the hydrophobic adsorbent comprises a phenyl or a hexyl crosslinked agarose;
   c) washing the hydrophobic adsorbent with an aqueous salt solution;
   d) eluting the target oligonucleotide with an eluting solution; and
   e) collecting the eluent comprising the target oligonucleotide;
wherein the product-related impurity comprises at least one N−1 impurity, thereby separating the target oligonucleotide from the product-related impurity.

2. The method of claim 1, wherein the salt is added to the mixture as aqueous salt solution or the salt is dissolved directly into the mixture, and wherein the flow rate of the wash step is slower than the loading flow rate.

3. The method of claim 1, wherein the eluting solution is selected from water, an aqueous salt solution, ethylene glycol, or propylene glycol or mixtures thereof.

4. The method of claim 1, wherein the elution collection is delayed such that is does not include the first 1-25%, 10-25% or 5-10% of the product elution peak or the last 1-25%, 5-10% or 10-25% of the product elution peak.

5. The method of claim 1, wherein the hydrophobic adsorbent is packed at a bed height of at least 15 cm.

6. The method of claim 1, wherein the target oligonucleotide comprises 15 to 25 nucleotides.

7. The method of claim 1, wherein the target oligonucleotide comprises nucleobases independently selected from the group consisting of 9-adeninyl, 9-guaninyl, 1-thyminyl (5-methyl-1-uracilyl), 1-cytosinyl, 9-hypoxanthinyl, 9-xanthinyl, 7-methyl-9-guaninyl, 7-deaza-9-purinyl, and 5-hydroxymethyl-1-cytosinyl.

8. The method of claim 1, wherein the target oligonucleotide comprises sugar that is optionally substituted; two non-geminal ring atoms are bridged to form a bicyclic nucleic acid (BNA); or a ring oxygen atom of the sugar is replaced with S, N(R), or $C(R_1)(R_2)$, wherein R is H or C1-C12 alkyl and combinations of these.

9. The method of claim 8, wherein the sugar is substituted at the 2' position with $O[(CH_2)_nO]_mCH_3$, $O(CH_2)$—$NH_2$, $O(CH_2)_nCH_3$, $O(CH_2)_nONH_2$, $OCH_2C(\!=\!O)N(H)CH_3$, or $O(CH_2)_nON[(CH_2)_nCH_3]_2$, where n and m are independently from 1 to about 10.

10. The method of claim 1, wherein the target oligonucleotide comprises RNA only, DNA only, or a combination of RNA and DNA.

11. The method of claim 1, wherein the target oligonucleotide comprises phosphodiesters (P=O), phosphorothioates (β=S), or a combination thereof.

12. The method of claim 1, wherein the sequence of the target oligonucleotide is (SEQ ID NO: 1) or (SEQ ID NO: 2).

13. The method of claim 1, wherein the target oligonucleotide comprises 4,4'-dimethoxytrityl (DMT).

14. The method of claim 1, wherein the target oligonucleotide does not comprise 4,4'-dimethoxytrityl (DMT).

15. The method of claim 1, wherein the product related impurity further comprises at least one P=O impurity.

16. The method of claim 1, wherein the product related impurity further comprises at least one ABasic impurity or at least one CNEt impurity, or at least one N+1 impurity.

17. A method for separating a target oligonucleotide from a mixture containing the target thiolated oligonucleotide and a product-related impurity, the method comprising the steps of:
   a) adding a salt to the mixture, wherein the salt is ammonium sulfate;
   b) contacting the diluted mixture with a hydrophobic adsorbent at a dynamic loading capacity of about 40 to about 100% of the capacity of the hydrophobic adsorbent, wherein the hydrophobic adsorbent comprises a phenyl or a hexyl crosslinked agarose;
   c) washing the hydrophobic adsorbent with an aqueous salt solution;
   d) eluting the target oligonucleotide with an eluting solution; and
   e) collecting the eluent comprising the target oligonucleotide;
   wherein the product-related impurity comprises at least one P=O impurity, thereby separating the target oligonucleotide from the product-related impurity.

18. The method of claim 17, wherein the product related impurity further comprises at least one N−1 impurity.

* * * * *

UNITED STATES PATENT AND TRADEMARK OFFICE
CERTIFICATE OF CORRECTION

PATENT NO.        : 10,947,262 B2
APPLICATION NO.   : 16/309622
DATED             : March 16, 2021
INVENTOR(S)       : Robert S. Gronke et al.

Page 1 of 1

It is certified that error appears in the above-identified patent and that said Letters Patent is hereby corrected as shown below:

In the Claims

At Column 16, Claim 9, Line 14, replace "O(CH$_2$)–NH$_2$" with:
-- O(CH$_2$)$_m$–NH$_2$ --; and At Column 16, Claim 11, Line 24, replace "(β=S)" with:
-- (P=S) --.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
tcactttcat aatgctgg                                                    18

<210> SEQ ID NO 2
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
caggatacat ttctacagct                                              20
```